United States Patent
Sheppard et al.

(10) Patent No.: US 7,485,747 B2
(45) Date of Patent: Feb. 3, 2009

(54) TWO STAGE OXIDATION PROCESS FOR THE PRODUCTION OF AROMATIC DICARBOXYLIC ACIDS

(75) Inventors: Ronald Buford Sheppard, Kingsport, TN (US); Charles Edwan Sumner, Jr., Kingsport, TN (US); Brent Alan Tennant, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/156,312

(22) Filed: May 28, 2002

(65) Prior Publication Data

US 2002/0183546 A1    Dec. 5, 2002

Related U.S. Application Data

(60) Provisional application No. 60/295,618, filed on Jun. 4, 2001.

(51) Int. Cl.
*C07C 51/16* (2006.01)
*C07C 51/42* (2006.01)

(52) U.S. Cl. ...................... 562/487; 562/416

(58) Field of Classification Search ............ 562/77, 562/485, 486, 487, 417, 416; 560/68; 424/464; 514/651, 649
See application file for complete search history.

(56) References Cited

U.S. PATENT DOCUMENTS

| | | | |
|---|---|---|---|
| 3,057,909 A | 10/1962 | Sebelist et al. | |
| 3,064,044 A | 11/1962 | Baldwin | |
| 3,452,088 A | 6/1969 | Olsen et al. | |
| 3,584,039 A * | 6/1971 | Meyer | 562/416 |
| 3,799,976 A * | 3/1974 | Nienburg et al. | 562/416 |

(Continued)

FOREIGN PATENT DOCUMENTS

| | | |
|---|---|---|
| EP | 0111784 B1 | 2/1986 |
| GB | 983677 A | 2/1965 |
| GB | 1152575 | 5/1969 |
| GB | 1358520 A | 7/1974 |

(Continued)

OTHER PUBLICATIONS

PCT International Search Report.

(Continued)

*Primary Examiner*—Taylor Victor Oh
(74) *Attorney, Agent, or Firm*—Steven A. Owen; Dennis V. Carmen; Bernard J. Graves, Jr.

(57) ABSTRACT

Disclosed is a process for producing a benzenedicarrboxylic acid such as terephthalic acid wherein a dialkyl benzene compound and acetic acid having catalyst components dissolved therein are fed to a first reaction zone wherein the dialkyl benzene compound is oxidized with molecular oxygen to provide a first oxidation zone product comprising a benzenedicarboxylic acid containing minor amounts of mono-carboxylic acid by-products such as carboxybenzaldehyde and toluic acid. The first oxidation zone product comprising a slurry of a benzenedicarboxylic acid containing minor amounts of mono-carboxylic acid by-products is fed to a second oxidation reaction zone that is operated under more severe conditions of temperature and pressure. The rate of the feed of a molecular oxygen containing gas to the second oxidation zone is about 3% or less of the the rate of the feed of the molecular oxygen containing gas to the first oxidation zone. The benzenedicarboxylic acid product obtained contains a total concentration of carboxybenzaldehyde and toluic acid of about 150 ppmw or less.

15 Claims, 1 Drawing Sheet

U.S. PATENT DOCUMENTS

| | | | |
|---|---|---|---|
| 3,850,983 | A | 11/1974 | Park |
| 3,931,305 | A | 1/1976 | Fisher |
| 3,996,271 | A | 12/1976 | Yokota et al. |
| 4,158,738 | A | 6/1979 | Scott et al. |
| 4,356,319 | A | 10/1982 | Roffia et al. |
| 4,438,279 | A * | 3/1984 | Packer et al. ............... 562/416 |
| 4,467,111 | A * | 8/1984 | Puskas et al. ............... 562/487 |
| 4,500,732 | A | 2/1985 | Petty-Weeks et al. |
| 4,772,748 | A | 9/1988 | Hashizume et al. |
| 4,892,970 | A | 1/1990 | Nowicki et al. |
| 4,939,297 | A | 7/1990 | Browder et al. |
| 5,095,146 | A | 3/1992 | Zeitlin et al. |
| 5,110,984 | A * | 5/1992 | Janulis ....................... 562/487 |
| 5,175,355 | A * | 12/1992 | Streich et al. ............... 562/485 |
| 5,510,521 | A | 4/1996 | McGehee et al. |
| 5,567,842 | A | 10/1996 | Izumisawa et al. |
| 5,583,254 | A | 12/1996 | Turner et al. |
| 5,763,648 | A | 6/1998 | Hashizume et al. |
| RE36,008 | E * | 12/1998 | Hindmarsh et al. ......... 562/414 |
| 6,297,348 | B1 | 10/2001 | Rodden et al. |
| 2002/0183546 | A1 | 12/2002 | Sheppard et al. |
| 2002/0193630 | A1 | 12/2002 | Lin et al. |
| 2004/0260052 | A1 | 12/2004 | Nagao et al. |

FOREIGN PATENT DOCUMENTS

| | | |
|---|---|---|
| GB | 1454478 A | 11/1976 |
| JP | 11343264 A | 11/1990 |
| JP | 2001247511 A | 9/2001 |
| JP | 2001-288139 A | 10/2001 |
| WO | WO 99/31038 | 6/1999 |

OTHER PUBLICATIONS

Arun Pal Aneja and Viney Pal Aneja, "The Effect of Water and Air Contamination on Poly(Ethylene Terephthalate) Formation", Polymer Engineering Reviews, 1982, pp. 123-133, vol. 2, No. 2.
Co-pending U.S. Appl. No. 10/161,571, filed May 31, 2002.
Co-pending U.S. Appl. No. 10/423,389, filed Apr. 25, 2003.
USPTO Office Action dated Nov. 27, 2007 for copending U.S. Appl. No. 11/254,406.
USPTO Notice of Allowance dated Dec. 26, 2007 for copending U.S. Appl. No. 11/254,406.
Copending U.S. Appl. No. 11/254,406, filed Oct. 20, 2005.
Copending U.S. Appl. No. 10/161,571, filed May 31, 2002.
Copending U.S. Appl. No. 10/423,389, filed Apr. 25, 2003.
USPTO Office Action dated Nov. 23, 2005 for U.S. Appl. No. 10/423,389.
USPTO Office Action dated Jul. 13, 2005 for U.S. Appl. No. 10/423,389.
USPTO Office Action dated Feb. 7, 2005 for U.S. Appl. No. 10/423,389.
USPTO Office Action dated Jun. 30, 2004 for U.S. Appl. No. 10/423,389.
USPTO Office Action dated Jun. 29, 2005 for U.S. Appl. No. 10/161,571.
USPTO Office Action dated Sep. 9, 2004 for U.S. Appl. No. 10/161,571.
USPTO Office Action dated Apr. 23, 2004 for U.S. Appl. No. 10/161,571.
USPTO Office Action dated Sep. 24, 2003 for U.S. Appl. No. 10/161,571.
USPTO Office Action dated Dec. 4, 2002 for U.S. Appl. No. 10/161,571.

* cited by examiner

TWO STAGE OXIDATION PROCESS FOR THE PRODUCTION OF AROMATIC DICARBOXYLIC ACIDS

CROSS REFERENCE TO RELATED APPLICATION

This application claims the benefit of U.S. Provisional Application Ser. No. 60/295,618 filed Jun. 4, 2001.

FIELD OF THE INVENTION

This invention pertains to a novel process for the production of benzenedicarboxylic acids such as terephthalic acid by the oxidation of a dialkyl benzene compound. More specifically, this invention pertains to an oxidation process wherein a dialkyl benzene compound is oxidized to a benzenedicarboxylic acid by means of a two-stage process utilizing certain conditions to obtain the benzenedicarboxylic acid having improved purity.

BACKGROUND OF THE INVENTION

Aromatic dicarboxylic acids are produced by the oxidation of dialkyl aromatics. Terephthalic acid (TPA) is commercially produced by the liquid phase oxidation of p-xylene in the presence of an oxidation catalyst such as a Co—Mn—Br and a solvent such as acetic acid. Isophthalic acid is produced by the oxidation of m-xylene. Both processes produce crude dicarboxylic acids containing colored impurities and monocarboxylic acids such as carboxybenzaldehyde, i.e., 4-carboxybenzaldehyde (4-CBA) for terephthalic acid and 3-carboxybenzaldehyde (3-CBA) for isophthalic acid, and toluic acid, p-toluic acid for terephthalic acid and m-toluic acid for isophthalic acid. To achieve, for example, purified terephthalic acid used in the production of polyester fibers, films, and resins, crude terephthalic acid is treated further to remove impurities present due to the partial or incomplete oxidation of p-xylene. Typical commercial processes remove impurities by isolating a crude terephthalic acid solid, dissolving the solid in water at elevated temperatures and pressures, hydrogenating the resultant solution, cooling and crystallizing the product out of solution, and separating the solid product from the liquid. Colored impurities (of the benzil, anthraquinone, and fluorenone families) are hydrogenated to colorless products which are either are present in the TPA product or are removed in the the wastewater streams. Monofunctional 4-carboxybenzaldehyde is hydrogenated to p-toluic acid, which is separated from the sold product in the crystallization section of the process.

U.S. Pat. No. 4,158,738 describes a process for the production of terephthalic acid by the two-stage oxidation of p-xylene at elevated temperatures. This process requires a primary oxidation at temperatures greater than 210° C. Significant amounts of acetic acid, typically used as a solvent in the oxidation process, is oxidized at this temperature together with the p-xylene. The oxidation produces methyl acetate and methane, which must be disposed of, and carbon dioxide. The secondary oxidation of the process described in U.S. Pat. No. 4,158,738 occurs at a temperature equal to or less than that of the primary oxidation. The primary oxidation produces a crystalline, crude TPA product containing colored impurities and 4-CBA contained within the TPA crystals where it is difficult for the impurities to be further oxidized to TPA. The secondary oxidation temperature proposed by U.S. Pat. No. 4,158,738 does not allow for adequate dissolution of crude TPA crystals, and thus does not allow for sufficient conversion of the partially oxidized intermediate impurities, e.g., 4-CBA and p-toluic acid, contained therein to TPA.

U.S. Pat. No. 4,772,748 discloses a process for producing TPA by means of four oxidation steps, one of which is conducted at a higher temperature than the primary oxidation step. This higher temperature oxidation step uses molecular oxygen. Each of the oxidation steps is carried out using excess oxygen by controlling the flow of the air or other oxygen-containing gas to the oxidizer. However, feeding excess oxygen results in excessive oxidation (burn) of acetic acid. Furthermore, because the process uses four oxidation steps to reach the targeted impurity level, capital equipment and operating costs are high.

BRIEF SUMMARY OF THE INVENTION

An improved two-stage oxidation process for the production of benzenedicarboxylic acids, e.g., terephthalic acid, has been developed. Our novel process provides a terephthalic acid containing less than about 150 parts per million be weight (ppmw), based on the weight of the TPA, 4-CBA while avoiding significant oxidation of the acetic acid solvent. The present invention provides a process for the production of a benzenedicarboxylic acid such as terephthalic acid containing less than a total of about 150 ppmw carboxybenzaldehyde and toluic acid which comprises the steps of:

(1) feeding (i) a dialkyl benzene compound, (ii) aqueous acetic acid reaction medium having oxidation catalyst components dissolved therein, and (iii) an oxygen-containing gas to a first pressurized oxidation zone wherein liquid-phase, exothermic oxidation of the dialkyl benzene compound occurs, wherein the temperature and pressure within the first pressurized oxidation reactor are maintained at about 150 to 180° C. and about 3.5 to 13 bars absolute—(about 50 to 189 pounds per square inch—psia);

(2) removing from the upper portion of the first reactor a vapor comprising vaporized aqueous, acetic reaction medium and oxygen-depleted gas comprising carbon dioxide, methane, inert components, and less than about 9 volume percent, based on the non-condensable components of the vapor, oxygen;

(3) removing from the lower portion of the first reactor an oxidizer product comprising (i) solid and dissolved benzenedicarboxylic acid and incomplete oxidation products and (ii) the aqueous, acetic acid reaction medium having the oxidation catalyst dissolved therein;

(4) feeding (i) the oxidizer product of step (3) and (ii) an oxygen-containing gas to a second pressurized oxidation zone wherein liquid-phase, exothermic oxidation of the incomplete oxidation products occurs, wherein the temperature and pressure within the second pressurized oxidation reactor are maintained at about 185 to 230° C. and about 4.5 to 18.3 bar (about 65 to 265 psia);

(5) removing from the upper portion of the second reactor a vapor comprising vaporized aqueous, acetic reaction medium and oxygen-depleted gas comprising carbon dioxide, methane, inert components, and less than about 5 volume percent, based on the non-condensable components of the vapor, oxygen;

(6) removing from the lower portion of the second reactor a second oxidizer product comprising (i) solid and dissolved benzenedicarboxylic acid and (ii) the aqueous, acetic acid reaction medium having the oxidation catalyst dissolved therein; and (7) separating the benzenedicarboxylic acid from the (ii) the aqueous, acetic acid reaction medium of step (6) to obtain the benzenedicarboxylic acid containing less than about 150 ppmw carboxyaldehyde and toluic acid.

BRIEF DESCRIPTION OF THE DRAWINGS

Accompanying

DETAILED DESCRIPTION

Figure 1:
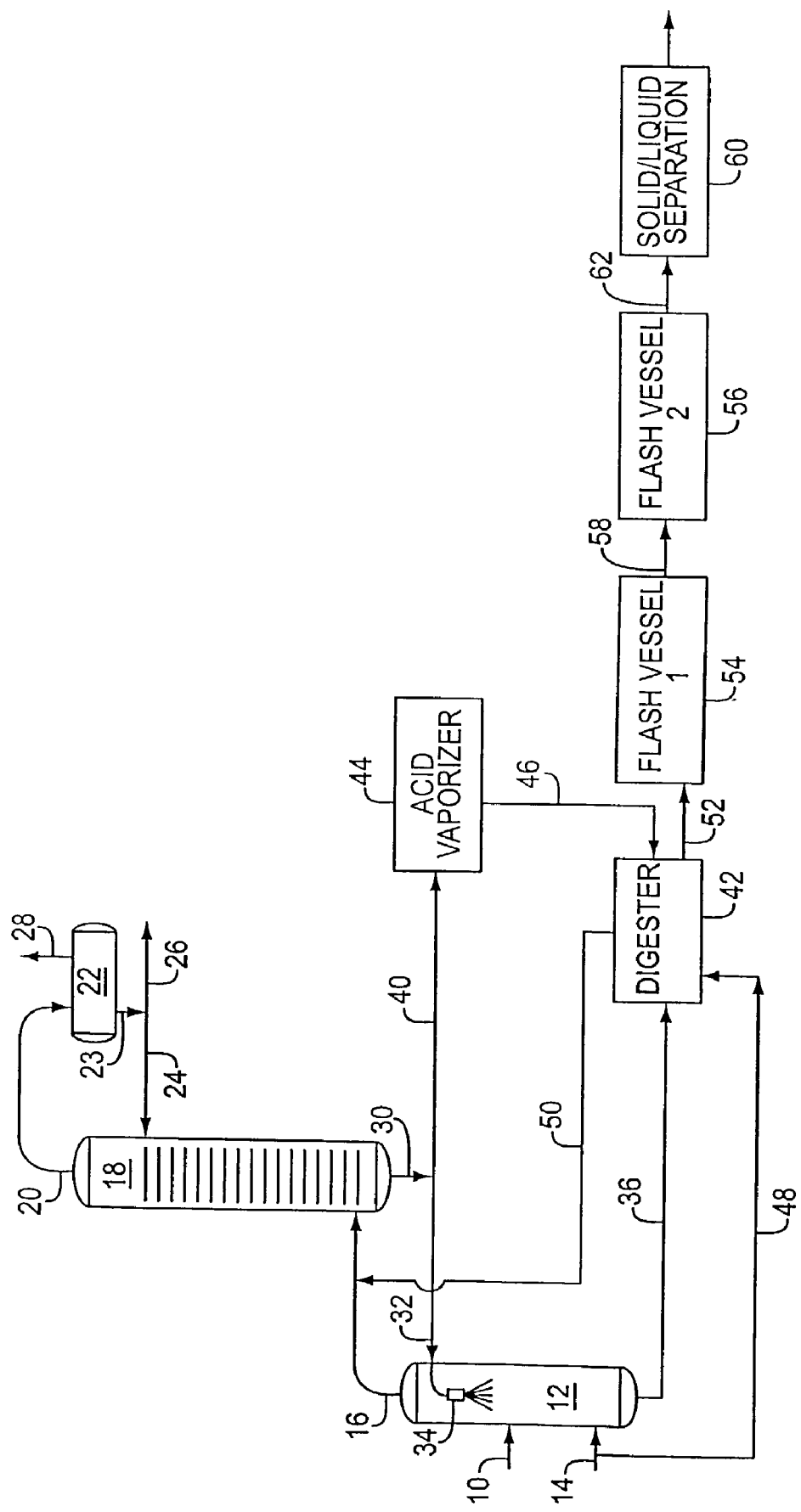
FIG. 1 is a process flow diagram illustrating a system embodying the principles of the process of the present invention. While the present invention is susceptible to embodiment in various forms, there is shown in accompanying FIG. 1 and hereinafter described in detail a preferred embodiment of the invention. The present disclosure is to be considered as an exemplification of the invention without limitation to the specific embodiment illustrated, however.

Referring to accompanying FIG. 1, step (1) of our novel process may be carried out in a first oxidation zone comprising reactor vessel 12. A feed mixture comprising a dialkyl benzene compound, aqueous acetic acid, and a suitable oxidation catalyst are fed to first oxidation reactor 12 via conduit 10. The acetic acid reaction medium or solvent feed typically contains up to about 15 weight percent water. If desired, the dialkyl benzene compound and/or acetic acid solvent containing catalyst components may be fed to reactor 12 at a plurality of points along the side of the reactor 12. A molecular oxygen-containing gas under pressure is introduced via conduit 14 to reactor 12 is continuously fed at or near the base of the columnar reaction vessel. The oxygen-containing gas, e.g., oxygen, oxygen-enriched air or, preferably, air, normally is fed at or near the base of the columnar reaction vessel. The flow rate of the oxygen-containing gas to reactor 12 is controlled to maintain between about 2 and 9, preferably about 2 to 5, volume percent oxygen (calculated on a dry, solvent free basis) in the off-gas which exits the reactor via conduit 16. The reactants in reactor 12 are maintained at an elevated pressure sufficient to maintain the contained, volatilizable reaction medium substantially in the liquid state at the reaction temperature. The temperature and pressure within reactor 12 are about 150 to 180° C. and about 3.5 to 13 bar (about 50 to 189 psia) preferably about 155 to 165° C. and about 5.2 to 6.9 bar (about 75 to 100 psia).

Reactor 12 typically is a columnar, pressurized, oxidation reactor vessel wherein liquid-phase exothermic oxidation of the dialkyl aromatic compound by the oxygen-containing gas takes place in the presence of the oxidation catalyst. The first oxidation zone may comprise a single reactor or a plurality of reactors arranged in parallel. The reaction medium contained by reactor 12 thus comprises the oxygen-containing gas, the dialkyl benzene compound that is to be oxidized to an benzenedicarboxylic acid product, the catalyst, and the aqueous, acetic acid solvent. The amount of water present normally does not exceed about 15 weight percent, preferably about 4 to 6 weight percent, based on the weight of the water and the acetic acid. Typically, the generally-cylindrical, first oxidation vessel has a height:diameter ratio in the range of about 3 to 20.

The catalyst systems which may be employed in the oxidation process include any catalyst system conventionally used for liquid-phase oxidation of an alkyl aromatic hydrocarbon. A suitable catalyst system comprises a mixture of cobalt, manganese and bromine compounds or complexes, soluble in aqueous acetic acid. The atomic ratio of the Co:Mn:Br combination of catalyst elements preferably is in the range of about 5 to 40:1.0:4 to 40, more preferably a Co:Mn:Br atomic ratio of about 16 to 40:1.0:16 to 40.

During the course of the oxidation reaction, exothermic heat of reaction, generated by the oxidation of the dialkyl benzene compound, is removed from reactor 12 by vaporization of a portion of the liquid reaction medium. In accordance with step (2) of the present process, the vaporized liquid reaction medium (off-gas), along with the oxygen-depleted process gas containing minor amount of decomposition products and bromine-containing compounds, pass upwardly through reactor 12 and are introduced via conduit 16 into a condenser system such as water column 18. The condensable components of the vapors collected in column 18 consist primarily of the acetic acid solvent which is returned to reactor 12 via conduits 30 and 32 and spray head 34.

As shown in FIG. 1, overhead aqueous vapors exit the upper portion of water removal column 18 through conduit 20 and fed to condenser 22. The composition of the condesable components of the aqueous vapors collected in condenser 22, known as the distillate, is greater than 99 weight percent water. A portion of the distillate is returned as reflux to the fractionating zone of column 18 via conduits 23 and 24. The remainder of the distillate is removed for disposal via conduits 23 and 26. The non-condensable components are vented via conduit 20 from the production system or may be transported to a pollution control device for further treatment, if desired.

A distilled bottoms liquid comprising partially dewatered acetic acid solvent, e.g., acetic acid containing about 4 to 12 weight percent water, exits the lower portion of the water removal column 18 via conduit 30. A portion of the partially de-watered solvent is recycled directly to the reactor 12 via conduit 32. This amount ranges from about 10 to 100 percent. The partially de-watered solvent is fed to the reactor 12 by one or more spray nozzles 34, which may be located below exit conduit 16 and above the phase separation of the gas/liquid contents of the reactor 12. Another portion of the partially de-watered solvent is removed via conduit 40. Some or all of the condensed acetic acid may be returned to reactor 12 via feed stream 10.

In operation, first pressurized oxidation reactor 12 produces a benzenedicarboxylic acid product that is sparingly soluble in the process solvent and is removed through a lower exit port located at or near the base of the reactor as a slurry in the solvent which also contains dissolved catalyst components. The oxidation process in reactor 12 also produces by-products such as mono-carboxylic acids such as carboxybenzaldehyde and toluic acid. At least a portion of these mon-carboxylic acids are solids which, as mentioned above, may be contained within the crystals of the benzene dicarboxylic acid. These mono-functional compounds are undesirable by-products since they function as polymer chain terminators and thus can result in the formation of low molecular weight polyesters such as poly(ethylene terephthalate) produced from terephthalic acid and ethylene glycol.

In accordance with steps (3) and (4) of our novel process, the slurry of benzenedicarboxylic acid product and mono-carboxylic acid by-products is continuously withdrawn as a slurry in the aqueous, acetic acid process solvent, which also contains dissolved catalyst, from the bottom portion of reactor 12 and conveyed via conduit 36 to a second pressurized oxidation zone shown in FIG. 1 as reactor 42. The second oxidation zone may be a single, agitated reactor as depicted in FIG. 1 or two or more agitated reactors may be arranged in series or parallel. The aqueous acetic acid solvent typically contains about 5 to 12 weight percent water, based on the weight of the water and the aliphatic, carboxylic acid. A molecular oxygen-containing gas also is fed to second oxidation reactor 42 wherein the carboxybenzaldehyde and toluic acid by-product are further oxidized to the desired benzene dicarboxylic acid. As in the case of the fed to the first oxidation reactor, the oxygen-containing gas may be oxygen, oxygen-enriched air or, preferably, air. The oxygen-containing gas normally is fed at or near the base of second oxidation reactor 42 below the surface of the liquid contents of the reactor.

The flow rate of the oxygen-containing gas to reactor 42 may be controlled to maintain between 0 and about 5, preferably about 0 to 1, volume percent oxygen (calculated on a dry, solvent free basis) in the off-gas which exits the reactor via conduit 50. The flow rate of oxygen-containing gas to reactor 42 normally is from 0.001 to 3 volume percent, preferably 0.001 to 2 volume percent, of the flow rate of oxygen-containing gas to reactor 12. The small amount of air fed to the second oxidation reactor 42 limits the oxidative decomposition of the acetic acid solvent, yet facilitates the conversion of the by-product mono-carboxylic acids to the desired benzene dicarboxylic acid.

The first oxidizer reactor described above accomplishes substantially all of the oxidation while operating at moderate pressure and temperature. The primary obstacle in achieving sufficient conversion of the dialkyl benzene compound to the benzenedicarboxylic acid in the primary oxidizer system is mass transfer limitations associated with oxygen diffusion to the partially oxidized products embedded or contained in the benzenedicarboxylic acid, i.e., the partially oxidized, mono-carboxylic acid by-products may be encased within aromatic dicarboxylic acid crystals. Therefore, it is relatively easy to oxidize most of the dialkyl benzene compound to a benzene-dicarboxylic acid even under moderate conditions. However, to achieve sufficiently complete conversion requires overcoming the mass transfer limitations. Operation of the first oxidation zone under moderate conditions of pressure and temperature can aid in the formation of small or fine crystals that can be dissolved and recrystallized in the second oxidation zone. When the small or fine crystals are dissolved in the second oxidation zone, the co-crystalizaed by-products are accessible for further oxidation.

The materials in second oxidation reactor 42 are maintained at an elevated pressure sufficient to maintain the contained, volatilizable reaction medium substantially in the liquid state at the reaction temperature. The temperature and pressure within reactor 12 are about 185 to 230° C. and about 4.5 to 18.3 bar (about 65 to 265 psia), preferably about 205 to 215° C. and about 13.4 to 17.2 bar (about 195 to 250 psia). The heat required for the operation of the second oxidation zone may be provided by supplying a vapor phase solvent to the second oxidation reactor and allowing the vapor phase solvent to condense. The vapor phase solvent normally will be at a pressure sufficient to allow the vapor to pass into the second oxidation reactor and to provide sufficient heat to the contents of the second oxidation reactor. For example, partially de-watered acetic acid may be fed from water removal column 18 to acid vaporizer 44 via conduits 30 and 40. The acid vaporizer 44 brings the partially de-watered acetic acid to a temperature and pressure sufficient to maintain the desired temperature within the second oxidation reactor 42. The design of the acetic acid vaporizer normally requires the availability of a heat transfer fluid such as Dowtherm or high pressure steam can be used to vaporize the acetic acid. The acetic acid vapor is transferred from the acid vaporizer 44 to second oxidation reactor 42 via conduit 46.

An off-gas stream comprising vaporized liquid reaction medium along with the oxygen-depleted process gas containing minor amount of decomposition products and bromine-containing compounds is removed from the upper section or top of second oxidation reactor 42 and fed via conduits 50 and 16 to a condenser system such as water column 18. The condensable components of the off-gas stream consisting primarily of acetic acid solvent may be recovered as described above.

The benzenedicarboxylic acid product is removed from second oxidation reactor 42 as a slurry in the aqueous, acetic acid process solvent, which also contains dissolved catalyst components via conduit 52. The slurry removed from reactor 42 typically comprises from about 20 to 40 weight percent solids and contains less than a total of about 150 based on the weight of the solids present, of incomplete oxidation products, primarily carboxybenzaldehyde and toluic acid. The total concentration of carboxybenzaldehyde plus toluic acid typically is in the range of about 50 to 150.

The slurry product from the second oxidation reactor 42 may be cooled before being introduced into a solid/liquid separation and, optionally, a solid drying system. Preferably, the slurry product from the second oxidation reactor 42 is fed to a flash evaporation zone wherein the temperature and pressure of the second oxidizer product are reduced by flash evaporation. The flash evaporation zone may comprise one or, preferably, a plurality of flash vessels wherein the slurry product is cooled by staged or sequential pressure reduction evaporation. As shown in FIG. 1, to cool the slurry, conduit 52 leads to a first flash vessel 54. From there, conduit 58 leads to a second flash vessel 56. The first and second flash vessels 54 and 56 provide for a staged pressure reduction from reactor 42. This staged or sequential pressure reduction serves two purposes. First, it eliminates the need for pumping between the units. Second, the adiabatic flash from the pressure reduction between reactor 42 and first flash vessel 54 allows for the first flash vessel 54 to act as an evaporative crystallizer. The average size of the crystals of benzenedicarboxylic acid crystals may increase in the first flash vessel 54. Vapor from both flash vessels 54 and 56 may be routed to a condenser (not shown). First flash vessel 54 may be operated at a temperature of about 170 to 190° C. and a pressure of about 2.4 to 5.2 bar (about 35 to 75 psia). The slurry stream from first flash vessel 54 is fed to second flash vessel 56, which is another adiabatic flash tank at temperatures from 60 to 100° C. and a pressure of 0.3 to 0.8 bar (about 5 to 12 psia). Although two flash vessels are shown in FIG. 1 for cooling and crystallization, either less than or more than two may be employed or another cooling method may be used.

The cooled slurry is conveyed via conduit 62 to solid/liquid separation zone 60 wherein the solid benzenedicarboxylic acid is separated from the aqueous acetic acid solvent/reaction medium using conventional liquid/solid separation means. After separation, the cake of the benzenedicarboxylic acid is washed, for example, with cooled acetic acid from the water removal column 18. The wet filter cake may be dried to evaporate the residual acetic acid from the cake. A dried product is obtained from the solid/liquid separation device 60. The composition of this product is essentially the same as the composition of the solids present in the slurry product from second reaction zone 42.

p-Xylene and m-xylene are examples of suitable dialkyl benzene compounds useful as reactor feed materials in the process of the present invention to produce terephthalic acid and isophthalic acid, respectively. The process is particularly useful for the production of IPA and, especially, TPA.

EXAMPLE

The process of our invention is further illustrated by the following example wherein parts of materials are parts by weight. p-Xylene and acetic acid having a Co/Mn/Br catalyst system dissolved therein was fed to the side of first oxidation reactor 18 through conduit 10 while air was fed to the base of the reactor via conduit 14. Aqueous acetic acid containing dissolved catalyst was fed at a rate of 3.1 parts per minute and p-xylene was fed at the rate of 0.45 parts per minute via conduit 10 to reactor 12 which consisted of a cylindrical pressure vessel having a height:diameter ratio of 13.3. Air was fed via conduit 14 at a rate of 2.0 parts per minute. The gas/liquid oxidation reaction mixture filled approximately 85% of the volume of the reactor. The temperature of the vigorously mixed reaction mixture was 160° C. and the pressure was controlled at 6.2 bar absolute (90 psig). Oxidizer product consisting of a slurry of 30 weight percent TPA in aqueous acetic acid containing dissolved catalyst was removed from the base of the reactor via line 36 at the rate of 2.4 parts per minute. A vapor stream comprising oxygen-depleted air, acetic acid and water was removed continuously via a port located at the top of the sidewall of the reactor and transported via conduit 16 to water column 18. A portion of the condensate was recycled directly to the reactor via conduits 30 and 32 and spray head 34.

Oxidizer product comprising terephthalic acid, p-carboxybenzaldehyde and p-toluic acid in acetic acid containing dissolved catalyst component was removed from first oxidation reactor 18 via conduit 36 and fed to stirred second oxidation reactor 42 operated at 209° C. and 15.5 bar (225 psia). Air was fed to second oxidation reactor 42 at a rate which was approximately 3% of the air flow fed to first reactor 12. An off-gas containing about 0.5 volume percent oxygen was removed from second oxidation reactor 42. The product from the digester was then cooled, separated and washed using a rotary vacuum filter. The TPA product obtained contained 110 ppm 4-CBA and 8 ppm p-toluic acid, suitable for producing PET polymer and copolymer products.

While the invention has been described in detail with respect to specific embodiments thereof, it will be appreciated that those skilled in the art, upon attaining an understanding of the forgoing may readily conceive of alterations to, variations of and equivalents to these embodiments. Accordingly, the scope of the present invention should be assessed as that of the appended claims and any equivalents thereto.

We claim:

1. A process for reducing the content of 4-carboxybenzaldehyde and p-toluic acid in a benzene dicarboxylic acid composition comprising terephthlatic acid and containing less than a total of about 150 ppmw 4-carboxybenzaldehyde and p-toluic acid comprising:
   (1) feeding (i) paraxylene, (ii) aqueous acetic acid medium having an oxidation catalyst comprising a source of cobalt, a source of manganese, and a source of bromine dissolved therein, and (iii) an oxygen-containing gas to a first pressurized oxidation zone wherein liquid-phase, exothermic oxidation of paraxylene occurs, wherein the temperature and pressure within the first pressurized oxidation reactor are maintained at conditions of about 150 to 165° C. and about 3.5 to 13 bars absolute (bara) to produce an oxidizer composition comprising (i) dissolved terephthalic acid and terephthalic acid solids having the by-products 4-carboxybenzaldehyde and p-toluic acid, and (ii) an aqueous, acidic reaction medium having the oxidation catalyst composition dissolved therein;
   (2) removing from the upper portion of the first reactor a vapor comprising vaporized aqueous, acetic reaction medium and oxygen-depleted gas;
   (3) removing from the lower portion of the first reactor said oxidizer composition;
   (4) feeding (i) the oxidizer composition of step (3) and (ii) an oxygen-containing gas to a second pressurized oxidation zone wherein liquid-phase, exothermic oxidation of 4-carboxybenzaldehyde and p-toluic acid occurs, wherein the temperature and pressure within the second pressurized oxidation reactor are maintained at about 185 to 230° C. and about 4.5 to 18.3 bara, wherein the conditions in said first pressurized oxidation zone are effective to produce terephthalic acid solids containing said by-products that are accessible to further oxidation in said second pressurized oxidation reactor to provide a 4- carboxybenzaldehyde and p-toluic acid content of less than 150 ppmw in step (7) below;
   (5) removing from the upper portion of the second reactor a vapor comprising vaporized aqueous, acetic reaction medium and oxygen-depleted gas;
   (6) removing from the lower portion of the second reactor a second oxidizer composition comprising (i) solid and dissolved terephthalic acid and (ii) the aqueous, acetic acid reaction medium having the oxidation catalyst composition dissolved therein; and
   (7) separating terephthalic acid from the (ii) aqueous, acetic acid reaction medium of step (6) to a obtain terephthalic acid composition containing less than about 150ppmw 4-carboxybenzaldehyde and p-toluic acid.

2. Process according to claim 1 wherein step 1 is carried out at about 155 to 165° C. and about 5.2 to 6.9 bara in the presence of aqueous acetic acid reaction medium containing about 4 to 5 weight percent water having an oxidation catalyst comprising cobalt, manganese and bromine dissolved therein; and the second pressurized oxidation zone of step (4) are maintained at a temperature and pressure of about 205 to 215° C. and about 13.4 to 17.2 bara.

3. Process according to claim 2 wherein the atomic ratio of Co:Mn:Br is about 5 to 40:1.0:4 to 40.

4. Process according to claim 1 wherein the second oxidizer composition of step (6) are fed to a flash evaporation zone wherein the temperature and pressure of the second oxidizer composition are reduced by flash evaporation.

5. Process according to claim 1 wherein the second oxidizer composition of step (6) is fed to a flash evaporation zone comprising (i) a first flash vessel operated at a temperature of about 170 to 190° C. and a pressure of about 2.4 to 5.2 bara and (ii) a second flash vessel operated at a temperature of about 60 to 100° C. and a pressure of about 0.3 to 0.8 bara, wherein the temperature and pressure of the second oxidizer composition are reduced by flash evaporation.

6. A process comprising:
   (1) oxidizing paraxylene in the presence of an oxygen containing gas, an oxidation catalyst comprising a source of cobalt, a source of manganese and a source of bromine, and acetic acid solvent in a first pressurized oxidation reactor to produce an oxidation composition wherein the temperature within the first pressurized oxidation reactor is maintained at a temperature in the range of from about 150 to about 165° C.;
   (2) removing the oxidation composition from the first pressurized oxidation reactor and feeding the oxidation composition of step (1) to a second oxidation reactor; and
   (3) further liquid phase oxidizing in said second oxidation reactor said oxidation composition while feeding to said second oxidation reactor a vapor phase solvent comprising acetic acid and while maintaining the temperature within said second oxidation reactor at a temperature higher than the temperature within the first oxidation reactor and within a range of about 185-230° C.

7. The process of claim 6, wherein at least part of the 185-heat required for operating the second oxidation reactor at a temperature of about 230° C. is supplied by said vapor phase solvent.

8. The process of claim 6, wherein said vapor phase solvent is fed to said second oxidation reactor at a pressure sufficient to allow the vapor to pass into said second oxidation reactor and condense, while providing sufficient heat to the contents of the second oxidation reactor to maintain the temperature at about 185-230° C.

9. The process of claim 8, wherein said vapor phase solvent comprises acetic acid solvent.

10. The process of claim 9, wherein said acetic acid solvent comprises a partially dewatered acetic acid solvent.

11. The process of claim 6, wherein said vapor phase solvent comprises acetic acid solvent.

12. A process for the production of a benzenedicarboxylic composition comprising terephthalic acid, said process comprising:
   (1) feeding (i) p-xylene, (ii) an aqueous acetic acid reaction medium having an oxidation catalyst comprising a source of cobalt, a source of manganese, and a source of bromine dissolved therein, and (iii) an oxygen-containing gas to first pressurized oxidation zone wherein liquid-phase, exothermic oxidation of the p-xylene compound occurs wherein the temperature and pressure within the first pressurized oxidation reactor are maintained at about 150 to 165° C. and about 3.5 to 13 bars absolute (bara);
   (2) removing from the first reactor a vapor comprising vaporized aqueous, acetic reaction medium and oxygen-depleted gas;
   (3) removing from the first reactor an oxidizer composition comprising (i) terephthalic acid solids having a size, said solids having 4-carboxybenzaldehyde, and dissolved terephthalic acid, and 4-carboxybenzaldehyde, and (ii) the aqueous, acetic acid reaction medium having the oxidation catalyst dissolved therein;
   (4) feeding (i) the terephthalic acid solids having said size, the terephthalic acid, and 4-carboxybenzaldehyde produced in step (3), (ii) an oxygen-containing gas, and (iii) a vapor phase solvent to a final pressurized oxidation zone wherein liquid-phase, exothermic oxidation of 4-carboxybenzaldehyde occurs, wherein temperature and pressure within the final pressurized oxidation reactor are maintained at about 185-230° C. and about 4.5 to 18.3 bara;
   (5) removing from the final pressurized oxidation reactor a final oxidizer composition comprising solid and dissolved terephthalic acid and aqueous acetic acid reaction medium, and
   (6) separating the terephthalic acid from the aqueous acid reaction medium of step (5).

13. The process of claim 12, wherein said vapor solvent fed to the final pressurized oxidation reactor comprises an acetic acid solvent.

14. The process of claim 13, wherein said vapor solvent comprises a partially de-watered acetic acid solvent.

15. The process of claim 14, comprising feeding the removed vapor from said first reactor in step (2) to a water removal column, removing a distilled bottoms liquid comprising partially de-watered acetic acid solvent from the water removal column, and feeding at least a portion of said partially dewatered acetic acid solvent removed from the water removal column to said final pressurized oxidation reactor.

* * * * *

UNITED STATES PATENT AND TRADEMARK OFFICE
CERTIFICATE OF CORRECTION

PATENT NO.       : 7,485,747 B2  
APPLICATION NO.  : 10/156312  
DATED            : February 3, 2009  
INVENTOR(S)      : Sheppard et al.

Page 1 of 1

It is certified that error appears in the above-identified patent and that said Letters Patent is hereby corrected as shown below:

Column 9, Line 4, Claim 7 "185-heat" should read --heat--;  
Column 9, Line 5, Claim 7 "about 230° C." should read --about 185-230° C.--.

Signed and Sealed this

Sixteenth Day of June, 2009

JOHN DOLL  
*Acting Director of the United States Patent and Trademark Office*